(12) United States Patent
Shuros et al.

(10) Patent No.: US 8,905,999 B2
(45) Date of Patent: Dec. 9, 2014

(54) METHOD AND APPARATUS FOR ENDOLYMPHATIC DRUG DELIVERY

(75) Inventors: Allan C. Shuros, St. Paul, MN (US); Andrew P. Kramer, Stillwater, MN (US); Tamara Colette Baynham, Blaine, MN (US); James Cawthra, Ramsey, MN (US); M. Jason Brooke, Minneapolis, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 1964 days.

(21) Appl. No.: 11/469,793

(22) Filed: Sep. 1, 2006

(65) Prior Publication Data

US 2008/0097412 A1 Apr. 24, 2008

(51) Int. Cl.
*A61K 9/22* (2006.01)
*A61M 25/10* (2013.01)
*A61M 5/142* (2006.01)
*A61N 1/05* (2006.01)
*A61M 25/00* (2006.01)

(52) U.S. Cl.
CPC ....... *A61M 5/14276* (2013.01); *A61M 25/1011* (2013.01); *A61M 2025/0063* (2013.01); *A61M 1/36135* (2013.01); *A61M 2202/0405* (2013.01); *A61M 2025/0057* (2013.01); *A61N 1/056* (2013.01)
USPC ......................................... 604/890.1; 604/131

(58) Field of Classification Search
USPC ................ 604/890.1–892.1, 131, 151, 96.01, 604/164.01, 523
See application file for complete search history.

(56) References Cited

U.S. PATENT DOCUMENTS

| 3,814,080 | A |   | 6/1974  | Norman              |           |
|-----------|---|---|---------|---------------------|-----------|
| 3,916,875 | A |   | 11/1975 | Toch                |           |
| 4,650,467 | A | * | 3/1987  | Bonello et al.      | 604/95.04 |
| 4,792,330 | A |   | 12/1988 | Lazarus et al.      |           |
| 4,909,787 | A | * | 3/1990  | Danforth            | 604/95.03 |
| 4,957,484 | A |   | 9/1990  | Murtfeldt           |           |
| 5,112,303 | A | * | 5/1992  | Pudenz et al.       | 604/891.1 |
| 5,231,988 | A |   | 8/1993  | Wernicke et al.     |           |
| 5,284,153 | A |   | 2/1994  | Raymond et al.      |           |
| 5,305,745 | A |   | 4/1994  | Zacouto             |           |
| 5,333,609 | A | * | 8/1994  | Bedingham et al.    | 600/339   |

(Continued)

FOREIGN PATENT DOCUMENTS

| EP | 1504778 A2 | 2/2005 |
|----|-----------|--------|
| JP | 3-55032   | 3/1991 |

(Continued)

OTHER PUBLICATIONS

U.S. Appl. No. 11/422,414, filed Jun. 6, 2006, Amelioration of Chronic Pain by Endolymphatic Stimulation.
U.S. Appl. No. 11/422,417, filed Jun. 6, 2006, Method and Device for Lymphatic System Monitoring.
U.S. Appl. No. 11/422,418, filed Jun. 6, 2006, Method and Apparatus for Gastrointestinal Stimulation via the Lymphatic System.
U.S. Appl. No. 11/422,421, filed Jun. 6, 2006, Method and Apparatus for Neural Stimulation via the Lymphatic System.

(Continued)

*Primary Examiner* — Kevn C Sirmons
*Assistant Examiner* — Phillip Gray
(74) *Attorney, Agent, or Firm* — Schwegman Lundberg & Woessner, P.A.

(57) ABSTRACT

Described herein are a method and apparatus for introducing instrumentation into the lymphatic system that can be used for physiological monitoring and/or delivery of therapy. Such instrumentation, for example, may include one or more sensors for measuring physiological variables and/or one or more instruments for delivering therapy that is adapted to be disposed within a lymphatic vessel.

20 Claims, 5 Drawing Sheets

(56) References Cited

U.S. PATENT DOCUMENTS

| | | | |
|---|---|---|---|
| 5,387,231 A | 2/1995 | Sporer | |
| 5,391,143 A | 2/1995 | Kensey | |
| 5,423,872 A | 6/1995 | Cigaina | |
| 5,596,988 A * | 1/1997 | Markle et al. | 600/353 |
| 5,655,548 A | 8/1997 | Nelson et al. | |
| 5,658,318 A | 8/1997 | Stroetmann et al. | |
| 5,817,138 A | 10/1998 | Suzuki | |
| 5,865,744 A | 2/1999 | Lemelson | |
| 5,891,084 A * | 4/1999 | Lee | 604/521 |
| 6,024,704 A | 2/2000 | Meador et al. | |
| 6,106,477 A | 8/2000 | Miesel et al. | |
| 6,115,637 A | 9/2000 | Lennox et al. | |
| 6,238,423 B1 | 5/2001 | Bardy | |
| 6,272,370 B1 | 8/2001 | Gillies et al. | |
| 6,292,695 B1 | 9/2001 | Webster, Jr. et al. | |
| 6,321,109 B2 | 11/2001 | Ben-Haim et al. | |
| 6,347,247 B1 | 2/2002 | Dev et al. | |
| 6,368,274 B1 | 4/2002 | Van Antwerp et al. | |
| 6,370,417 B1 | 4/2002 | Horbaschek et al. | |
| 6,475,223 B1 | 11/2002 | Werp et al. | |
| 6,535,764 B2 | 3/2003 | Imran et al. | |
| 6,542,776 B1 | 4/2003 | Gordon et al. | |
| 6,584,362 B1 | 6/2003 | Scheiner et al. | |
| 6,587,719 B1 | 7/2003 | Barrett et al. | |
| 6,606,523 B1 | 8/2003 | Jenkins | |
| 6,609,025 B2 | 8/2003 | Barrett et al. | |
| 6,611,715 B1 | 8/2003 | Boveja | |
| 6,615,084 B1 | 9/2003 | Cigaina | |
| 6,629,534 B1 | 10/2003 | St. Goar et al. | |
| 6,676,686 B2 | 1/2004 | Naganuma | |
| 6,678,557 B1 | 1/2004 | Tumey | |
| 6,684,104 B2 | 1/2004 | Gordon et al. | |
| 6,692,490 B1 | 2/2004 | Edwards | |
| 6,735,477 B2 | 5/2004 | Levine | |
| 6,741,882 B2 | 5/2004 | Schaffter et al. | |
| 6,804,558 B2 | 10/2004 | Haller et al. | |
| 6,826,428 B1 | 11/2004 | Chen et al. | |
| 6,835,194 B2 * | 12/2004 | Johnson et al. | 604/890.1 |
| 6,865,416 B2 | 3/2005 | Dev et al. | |
| 6,879,859 B1 | 4/2005 | Boveja | |
| 6,889,076 B2 | 5/2005 | Cigaina | |
| 6,893,429 B2 * | 5/2005 | Petersen | 604/537 |
| 6,895,278 B1 | 5/2005 | Gordon | |
| 6,918,873 B1 | 7/2005 | Millar et al. | |
| 6,950,707 B2 | 9/2005 | Whitehurst | |
| 6,970,741 B1 | 11/2005 | Whitehurst | |
| 6,974,448 B2 * | 12/2005 | Petersen | 604/537 |
| 7,167,751 B1 | 1/2007 | Whitehurst et al. | |
| 7,250,041 B2 | 7/2007 | Chiu et al. | |
| 7,295,877 B2 | 11/2007 | Govari | |
| 7,526,337 B2 | 4/2009 | Shuros et al. | |
| 7,606,622 B2 | 10/2009 | Reeve | |
| 7,616,991 B2 | 11/2009 | Mann et al. | |
| 7,620,454 B2 | 11/2009 | Dinsmoor et al. | |
| 7,734,341 B2 * | 6/2010 | Shuros | 607/2 |
| 7,769,427 B2 | 8/2010 | Shachar | |
| 7,774,055 B1 | 8/2010 | Min | |
| 7,873,401 B2 | 1/2011 | Shachar | |
| 7,894,906 B2 | 2/2011 | Shuros | |
| 7,966,057 B2 | 6/2011 | Macaulay | |
| 8,116,883 B2 | 2/2012 | Williams et al. | |
| 8,126,538 B2 | 2/2012 | Shuros et al. | |
| 2001/0007924 A1 | 7/2001 | Kamada et al. | |
| 2001/0037061 A1 | 11/2001 | Eckmiller et al. | |
| 2001/0041870 A1 | 11/2001 | Gillis et al. | |
| 2002/0016615 A1 | 2/2002 | Dev et al. | |
| 2002/0029037 A1 | 3/2002 | Kim | |
| 2002/0072780 A1 | 6/2002 | Foley | |
| 2002/0087192 A1 | 7/2002 | Barrett et al. | |
| 2002/0123674 A1 | 9/2002 | Plicchi et al. | |
| 2002/0156462 A1 * | 10/2002 | Stultz | 604/891.1 |
| 2002/0188253 A1 | 12/2002 | Gordon et al. | |
| 2003/0009202 A1 | 1/2003 | Levine | |
| 2003/0018247 A1 | 1/2003 | Gonzalez | |
| 2003/0036773 A1 | 2/2003 | Whitehurst et al. | |
| 2003/0055463 A1 | 3/2003 | Gordon et al. |
| 2003/0078623 A1 | 4/2003 | Weinberg et al. |
| 2003/0105506 A1 | 6/2003 | Krishnan et al. |
| 2003/0113303 A1 | 6/2003 | Schwartz |
| 2003/0114895 A1 | 6/2003 | Gordon et al. |
| 2003/0144708 A1 | 7/2003 | Starkebaum |
| 2003/0204185 A1 | 10/2003 | Sherman et al. |
| 2004/0015201 A1 | 1/2004 | Greenstein |
| 2004/0024428 A1 | 2/2004 | Barrett et al. |
| 2004/0039427 A1 | 2/2004 | Barrett et al. |
| 2004/0088022 A1 | 5/2004 | Chen |
| 2004/0102804 A1 | 5/2004 | Chin |
| 2004/0106953 A1 | 6/2004 | Yomtov et al. |
| 2004/0147976 A1 | 7/2004 | Gordon et al. |
| 2004/0158297 A1 | 8/2004 | Gonzalez |
| 2004/0162595 A1 | 8/2004 | Foley |
| 2004/0172080 A1 | 9/2004 | Stadler et al. |
| 2004/0172088 A1 | 9/2004 | Knudson |
| 2004/0172102 A1 | 9/2004 | Leysieffer |
| 2004/0193229 A1 | 9/2004 | Starkebaum et al. |
| 2004/0210118 A1 | 10/2004 | Letort |
| 2004/0230255 A1 | 11/2004 | Dobak, III |
| 2004/0243182 A1 | 12/2004 | Cohen et al. |
| 2005/0033376 A1 | 2/2005 | Whitehurst |
| 2005/0043675 A1 | 2/2005 | Pastore et al. |
| 2005/0043894 A1 | 2/2005 | Fernandez |
| 2005/0049472 A1 | 3/2005 | Manda |
| 2005/0065575 A1 | 3/2005 | Dobak |
| 2005/0070974 A1 | 3/2005 | Knudson et al. |
| 2005/0075678 A1 | 4/2005 | Faul |
| 2005/0075701 A1 | 4/2005 | Shafer |
| 2005/0075702 A1 | 4/2005 | Shafer |
| 2005/0080346 A1 | 4/2005 | Gianchandani et al. |
| 2005/0090873 A1 | 4/2005 | Imran |
| 2005/1008046 | 4/2005 | Jenkins et al. |
| 2005/0131486 A1 | 6/2005 | Boveja et al. |
| 2005/0143765 A1 | 6/2005 | Bachmann et al. |
| 2005/0149014 A1 | 7/2005 | Hauck et al. |
| 2005/0149157 A1 | 7/2005 | Hunter et al. |
| 2005/0187584 A1 | 8/2005 | Denker et al. |
| 2005/0222637 A1 | 10/2005 | Chen |
| 2005/0222638 A1 | 10/2005 | Foley et al. |
| 2005/0246006 A1 | 11/2005 | Daniels |
| 2005/0267440 A1 | 12/2005 | Herman et al. |
| 2005/0273060 A1 | 12/2005 | Levy et al. |
| 2005/0288729 A1 | 12/2005 | Libbus et al. |
| 2005/0288730 A1 | 12/2005 | Deem et al. |
| 2006/0020333 A1 | 1/2006 | Lashinski et al. |
| 2006/0030837 A1 | 2/2006 | McKenna et al. |
| 2006/0074453 A1 | 4/2006 | Kieval et al. |
| 2006/0149331 A1 | 7/2006 | Mann et al. |
| 2006/0259077 A1 | 11/2006 | Pardo et al. |
| 2007/0021731 A1 | 1/2007 | Garibaldi et al. |
| 2007/0027460 A1 | 2/2007 | Case et al. |
| 2007/0027484 A1 | 2/2007 | Guzman et al. |
| 2007/0027500 A1 | 2/2007 | Maschino et al. |
| 2007/0244520 A1 | 10/2007 | Ferren et al. |
| 2007/0255340 A1 | 11/2007 | Giftakis et al. |
| 2007/0270675 A1 | 11/2007 | Kane et al. |
| 2007/0282376 A1 | 12/2007 | Shuros |
| 2007/0282382 A1 | 12/2007 | Shuros et al. |
| 2007/0282386 A1 | 12/2007 | Shuros |
| 2007/0282390 A1 | 12/2007 | Shuros |
| 2008/0009719 A1 | 1/2008 | Shuros et al. |
| 2008/0058887 A1 | 3/2008 | Griffin et al. |
| 2008/0086185 A1 | 4/2008 | Amurthur et al. |
| 2009/0228059 A1 | 9/2009 | Shuros |
| 2010/0042170 A1 | 2/2010 | Shuros et al. |
| 2010/0217346 A1 | 8/2010 | Shuros |
| 2010/0227807 A1 | 9/2010 | Stossel et al. |
| 2011/0106202 A1 | 5/2011 | Ding et al. |

FOREIGN PATENT DOCUMENTS

| | | |
|---|---|---|
| JP | 6-113998 A | 4/1994 |
| JP | 2004-065529 A | 3/2004 |
| JP | 2004-524893 A | 8/2004 |
| JP | 2005-532878 A | 11/2005 |
| SU | 1074527 A1 | 2/1984 |

(56) References Cited

FOREIGN PATENT DOCUMENTS

| WO | WO-03028542 A2 | 4/2003 |
|---|---|---|
| WO | WO-93/14694 A1 | 8/2003 |
| WO | WO-03/098177 A2 | 11/2003 |
| WO | WO-2004/006795 A1 | 1/2004 |
| WO | WO-2004/032791 A2 | 4/2004 |
| WO | WO-2005/089863 | 9/2005 |
| WO | WO-2005/089863 A1 | 9/2005 |
| WO | WO-2005-107862 A1 | 11/2005 |
| WO | WO-2007/067690 A2 | 6/2007 |
| WO | WO-2007/146489 A2 | 12/2007 |
| WO | WO-2007/146493 A1 | 12/2007 |
| WO | WO-2007/146517 A2 | 12/2007 |
| WO | WO-2008/030344 A2 | 3/2008 |

OTHER PUBLICATIONS

U.S. Appl. No. 11/422,423, filed Jun. 6, 2006, Method and Apparatus for Introducing Endolymphatic Instrumentation.
Pulley, M. S., et al., "Intravenous, intralesional and endolymphatic administration of lymphokines in human cancer.", *Lymphokine Res.*, 5 Suppl 1, (1986), S157-63.
Shuros, Allan C., "Amelioration of Chronic Pain by Endolymphatic Stimulation", U.S. Appl. No. 11/422,414, filed Jun. 6, 2006, 15 Pages.
Shuros, Allan C., "Method and Apparatus for Gastrointestinal Stimulation Via the Lymphatic System", U.S. Appl. No. 11/422,418, filed Jun. 6, 2006, 35 Pages.
Shuros, Allan C., et al., "Method and Apparatus for Introducing Endolymphatic Instrumentation", U.S. Appl. No. 11/422,423, filed Jun. 6 2006, 23 Pages.
Shuros, Allan C., et al., "Method and Apparatus for Neural Stimulation Via the Lymphatic System", U.S. Appl. No. 11/422,421, filed Jun. 6, 2006, 35.
Shuros, Allan C., et al., "Method and Device for Lymphatic System Monitoring", U.S. Appl. No. 11/422,417, filed Jun. 6, 2006, 15 Pages.
"U.S. Appl. No. 11/422,417, Non-Final Office Action mailed Sep. 25, 2007", 7 pgs.
"U.S. Appl. No. 11/422,417, Non-Final Office Action mailed Apr. 21, 2008", 7 pgs.
"U.S. Appl. No. 11/422,417, Notice of Allowance mailed Dec. 12, 2008", 4 pgs.
"U.S. Appl. No. 11/422,417, Response filed Aug. 21, 2008 to Non Final Office Action mailed Apr. 21, 2008", 6 pgs.
"U.S. Appl. No. 11/422,417, Response filed Aug. 27, 2007 to Restriction Requirement mailed Jul. 25, 2007", 4 pgs.
"U.S. Appl. No. 11/422,417, Restriction Requirement mailed Jul. 25, 2007", 5 pgs.
"U.S. Appl. No. 11/422,417, Response filed Jan. 25, 2008 to Non-Final Office Action mailed Sep. 25, 2007", 7 pgs.
"U.S. Appl. No. 11/422,418, Non-Final Office Action mailed Sep. 15, 2008", 11 pgs.
"U.S. Appl. No. 11/422,418, Response filed Dec. 15, 2008 to Non-Final Office Action mailed Sep. 15, 2008", 12 pgs.
"U.S. Appl. No. 11/422,418, Response filed Apr. 27, 2009 to Restriction Requirement mailed Mar. 25, 2009", 6 pgs.
"U.S. Appl. No. 11/422,418, Restriction Requirement mailed Mar. 25, 2009", 7 pgs.
"U.S. Appl. No. 11/422,421, Non-Final Office Action mailed Dec. 10, 2008", 16 pgs.
"U.S. Appl. No. 11/422,421, Response filed Apr. 9, 2009 to Non Final Office Action mailed Dec. 10, 2008", 12 pgs.
"U.S. Appl. No. 11/422,423, Response filed Feb. 9, 2009 to Non-Final Office Action mailed Oct. 8, 2008", 8 pgs.
"U.S. Appl. No. 11/422,423, Non-Final Office Action mailed Jan. 10, 2008", 10 pgs.
"U.S. Appl. No. 11/422,423, Non-Final Office Action mailed Oct. 8, 2008", 9 pgs.

"U.S. Appl. No. 11/422,423, Response filed May 12, 2008 to Non-Final Office Action mailed Jan. 10, 2008", 12 pgs.
"U.S. Appl. No. 11/422,423, Non-Final Office Action mailed Jun. 1, 2009", 7 pgs.
"European Application No. 07797400.4, Office Action mailed Apr. 21, 2009", 3 pgs.
International Application No. PCT/US2007/018631, International Search Report mailed Mar. 25, 2008, 4 pgs.
International Application No. PCT/US2007/018631, Written Opinion mailed Mar. 25, 2008, 7 pgs.
"International Application No. PCT/US2007/068617, International Search Report mailed Mar. 10, 2008", 4 pgs.
"International Application No. PCT/US2007/068617, Written Opinion mailed Mar. 10, 2008", 8 pgs.
"Physician's Manual—VNS Therapy™ Lead Model 302", Copyright 2003, 2004, 2005 Cyberonics, Inc., Houston, TX, (Jul. 2005), 35 pgs.
"U.S. Appl. No. 11/422,423, Decision on Pre-Appeal Brief Request mailed May 24, 2011", 2 pgs.
"U.S. Appl. No. 11/422,423, Notice of Allowance mailed Oct. 18, 2011", 5 pgs.
"U.S. Appl. No. 11/422,423, Pre-Appeal Brief Request filed Apr. 11, 2011", 5 pgs.
"U.S. Appl. No. 12/430,211, Appeal Brief flied Aug. 8, 2012", 9 pgs.
"U.S. Appl. No. 12/430,211, Final Office Action mailed Dec. 9, 2011", 6 pgs.
"U.S. Appl. No. 12/430,211, Response filed Oct. 21, 2011 to Non Final Office Action mailed Jun. 23, 2011", 8 pgs.
"U.S. Appl. No. 12/604,233 , Response filed Jul. 9, 2012 to Non Final Office Action mailed Apr. 10, 2012", 14 pgs.
"U.S. Appl. No. 12/604,233, Non Final Office Action mailed Apr. 10, 2012", 14 pgs.
"U.S. Appl. No. 12/604,233, Notice of Allowance mailed Oct. 3, 2012", 11 pgs.
"U.S. Appl. No. 12/775,223, Non Final Office Action mailed Apr. 23, 2012", 11 pgs.
"U.S. Appl. No. 12/775,223, Response filed Sep. 18, 2012 to Non Final Office Action mailed Apr. 23, 2012", 13 pgs.
"Australian Application Serial No. 2007293445, First Examiners Report mailed Apr. 11, 2012", 1 pg.
"Japanese Application Serial No. 2009-514438, Office Action mailed Feb. 27, 2012", (w/ English Translation), 5 pgs.
"Japanese Application Serial No. 2009-514438, Response filed May 25, 2012 to Office Action mailed Feb. 27, 2012", (w. Engiish Translation of Amended Claims), 10 pgs.
"Japanese Application Serial No. 2009-514441, Office Action mailed Feb. 29, 2012", (w/ English Translation), 6 pgs.
"U.S. Appl. No. 11/422,423, Notice of Allowance mailed Jul. 6, 2011", 9 pgs.
"U.S. Appl. No. 12/430,2011, Non Final Office Action mailed Jun. 23, 2011", 16 pgs.
"U.S. Appl. No. 12/430,211, Final Office Action mailed Feb. 1, 2011", 13 pgs.
"U.S. Appl. No. 12/430,211, Response filed Jan. 3, 2011 to Non Final Office Action mailed Sep. 1, 2010", 10 pgs.
"U.S. Appl. No. 12/430,211, Response filed Jun. 1, 2011 to Final Office Action mailed Feb. 1, 2011", 7 pgs.
"U.S. Appl. No. 12/604,233, Advisory Action mailed May 3, 2011", 8 pgs.
"U.S. Appl. No. 12/604,233, Final Office Action mailed Feb. 15, 2011", 9 pgs.
"U.S. Appl. No. 12/604,233, Response filed Apr. 12, 2011 to Final Office Action mailed Feb. 15, 2011", 11 pgs.
"U.S. Appl. No. 12/604,233, Response filed Jun. 15, 2011 to Advisory Action mailed May 3, 2011 and Final Office Action mailed Feb. 15, 2011", 13 pgs.
"European Application Serial No. 07782375.5, Response filed May 11, 2011 to Office Action mailed Nov. 22, 2010", 6 pgs.

* cited by examiner

METHOD AND APPARATUS FOR ENDOLYMPHATIC DRUG DELIVERY

RELATED APPLICATIONS

This application is related to co-pending application Ser. No. 11/422,414, filed on Jun. 6, 2006; Ser. No. 11/422,417, filed on Jun. 6, 2006; Ser. No. 11/422,418, filed on Jun. 6, 2006; Ser. No. 11/422,421, filed on Jun. 6, 2006 and Ser. No. 11/422,423, filed on Jun. 6, 2006, the disclosures of which are hereby incorporated by reference.

FIELD OF THE INVENTION

This invention pertains to methods and systems for treating disease with implantable devices.

BACKGROUND

The lymphatic system and the cardiovascular system are closely related structures that are indirectly joined by a capillary system. The lymphatic system is important to the body's defense mechanisms by filtering out organisms that cause disease and by producing lymphocytes that attack foreign organisms and generate antibodies. It is also important for the distribution of fluids and nutrients in the body, because it drains excess fluids and protein from interstitial tissues. Fluid that seeps out of the blood vessels into the interstitial spaces of body tissues and other interstitial components are then absorbed by lymphatic capillaries to form lymph that flows back into the bloodstream through the lymphatic vessels. The terminal structures of the lymphatic vessels include the right lymphatic duct, which drains lymph fluid from the upper right quarter of the body above the diaphragm and down the midline, and the thoracic duct, located in the mediastinum of the pleural cavity which drains the rest of the body. Through the flow of blood in and out of arteries, into the veins, and through the lymph vessels and nodes, the body is able to eliminate the products of cellular breakdown and foreign body invasion.

SUMMARY

Described herein are a method and apparatus for delivering a drug to internal body locations via the lymphatic system. In one embodiment, an implantable device containing a drug reservoir and control circuitry therefore is connected to a drug delivery catheter that is adapted to be disposed within a lymphatic vessel. The implantable device may also be configured, by means of leads or wirelessly, to receive sensor signals for controlling the delivery of the therapy. The implantable device may also communicate with an external system or external control device via a telemetry link.

DETAILED DESCRIPTION

The lymphatic vessels are part of the body's circulatory system and serve as a pathway by which fluids can flow from the interstitial spaces into blood. Lymphatic vessels also communicate with lymph nodes and facilitate the body's immune function by transporting foreign antigens to the lymph nodes from the interstitial spaces. With few exceptions, such as the brain and central nervous system, all of the body's tissues communicate with lymphatic vessels. This makes the lymphatic system a convenient conduit for delivering drugs directly to selected internal body locations. (As the term is used herein, a drug is any chemical or biological substance intended to have a therapeutic or diagnostic effect.) As described below, an implantable device may be configured with a drug delivery apparatus and a catheter adapted for disposition within a lymphatic vessel that delivers the drug to a target location that is normally drained by the lymphatic vessel. The catheter may be equipped with an inflatable balloon or other occluding structure actuated by the implantable device that blocks the normal antegrade flow of lymphatic fluid and permits the therapeutic agent to be injected into the vessel and flow distally from the balloon and then retrogradely to the target location. Other embodiments may employ no occluding structure and deliver the therapeutic agent so that it flows in an antegrade direction. The device may be further configured with one or more sensing modalities to enable delivery of therapy in accordance with the physiological monitoring and/or with a magnetically or tactilely actuated switch to enable patient control of therapy delivery. The device may also be equipped with wireless telemetry capability to allow control of drug delivery via telemetry commands.

Figure 1:
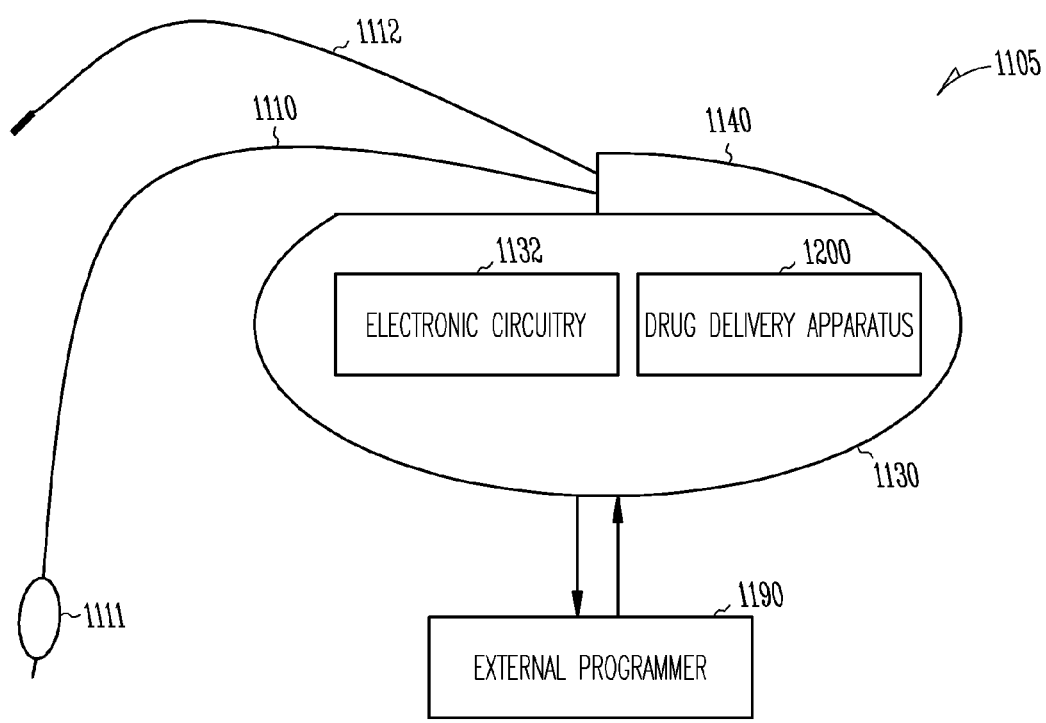
FIG. 1 shows an exemplary system for therapy delivery via the lymphatic system.

FIG. 1 shows an exemplary implantable drug delivery device that includes a delivery catheter adapted for disposition in a lymphatic vessel system to enable drug delivery via the lymphatic system. The implantable drug delivery device 1105 includes a hermetically sealed housing 1130 that may be placed subcutaneously or submuscularly in a patient's chest, similar to a cardiac pacemaker, or other convenient location. The housing 1130 may be formed from a conductive metal, such as titanium, and may additionally serve as an electrode for sensing electrical activity and/or delivering electrical stimulation. Contained within the housing 1130 is the electronic circuitry 1132 which may include a power supply and control circuitry for controlling the operation of the device (e.g., a programmable electronic controller or other types of logic circuitry). The electronic circuitry may also include sensing circuitry for sensing physiological variables and a telemetry transceiver for communicating with an external programmer 1190 or other external device such as a remote monitor or a wireless sensor. A header 1140 is mounted on the housing 1130 for receiving a drug delivery catheter 1110 which communicates with a drug delivery apparatus 1200 contained within the housing and controlled by the control circuitry. At the distal end of the catheter 1110 is an inflatable balloon 1111 that may be inflated by a balloon inflation apparatus within the housing through a lumen of the catheter to occlude lymphatic flow as described above. The header may also receive one or more leads 1112 having one or more electrodes or other types of sensors incorporated therein that may be used for sensing a physiological variable such as cardiac electrical activity and controlling the delivery of the drug in accordance therewith. In certain embodiments, the drug delivery device also incorporates cardiac rhythm management functionality, and a lead may be used to deliver electrical stimulation such as pacing or shock therapy.

Figure 2:
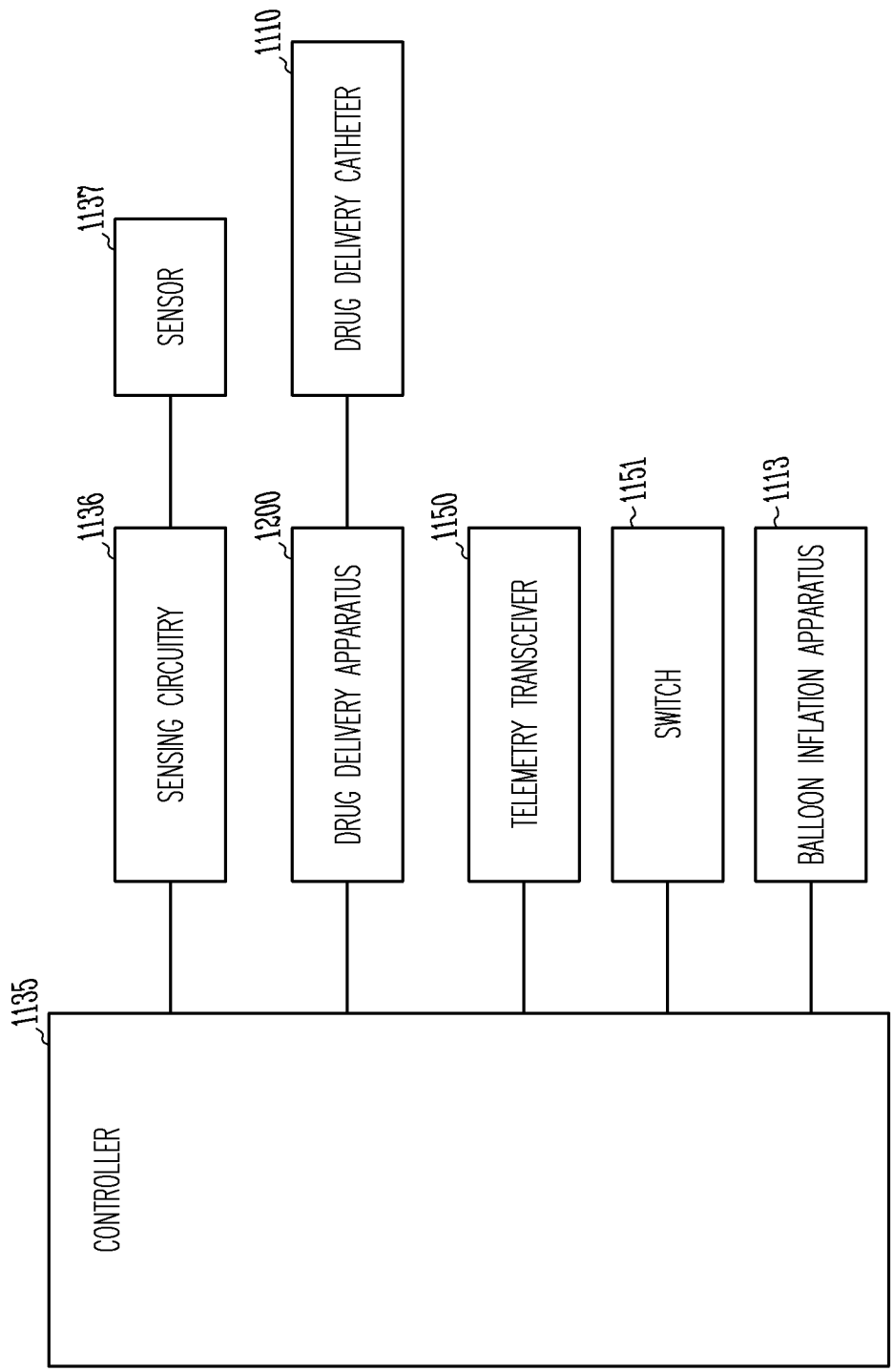
FIG. 2 illustrates exemplary components of the electronic circuitry depicted in FIG. 1.

FIG. 2 illustrates components of the electronic circuitry 1132 and drug delivery apparatus 1200 depicted in FIG. 1 according to one particular embodiment. A controller 1135 is provided which may be made up of discrete circuit elements but is preferably a processing element such as a microprocessor together with associated memory for program and data storage which may be programmed to perform algorithms for delivering therapy. (As the terms are used herein, "circuitry" and "controller" may refer either to a programmed processor or to dedicated hardware components configured to perform a particular task.) The controller is interfaced to the drug delivery apparatus 1200 which communicates with the catheter 1110 to effect delivery of a drug through the catheter to a target location. In one embodiment, the drug delivery apparatus is a mechanical pump with a reservoir for containing the drug, where the reservoir may be refillable after implantation. Pumping may also be accomplished in certain embodiments electronically, osmotically, or by electrophoresis. As aforesaid, the drug delivered by the device may be any type of therapeutic agent deliverable by the catheter such as a pain relieving agent, a cancer chemotherapeutic agent, an anti-inflammatory agent, an embolizing agent, a cardiac drug, an antibiotic agent, a gene therapeutic agent, and a biological cellular agent. The controller is also interfaced to sensing circuitry 1136 which receives signals generated by one or more sensors 1137. The controller may be configured to control the delivery of drugs by the device in response conditions or events in a closed-loop manner. The sensing circuitry may include, for example, circuitry for amplification, filtering, and/or analog-to-digital conversion of voltages generated by a sensor such as an electrode. As discussed above, in certain embodiments, the sensor 1137 may be an electrode attached to a lead that can be disposed in the heart for sensing cardiac electrical activity. In other embodiments, the sensor 1137 is a lymphatic sensor such as described in co-pending application Ser. No. 11/422,417 which may be incorporated into the catheter 1110, or a sensor located on the device housing.

Also interfaced to the controller in FIG. 2 is a telemetry transceiver 1150 capable of communicating with an external programmer 1190 or other external device as shown in FIG. 1. An external programmer wirelessly communicates with the device 1105 and enables a clinician to receive data and modify the programming of the controller. In the case where the device 1105 has sensing capability, a remote monitoring device similarly communicates with the device 1105 and may further interfaced to a network (e.g., an internet connection) for communicating with a patient management server that allows clinical personnel at remote locations to receive data from the remote monitoring device as well as issue commands. The controller may be programmed such that when particular conditions are detected by the sensing circuitry (such as when a measured parameter exceeds or falls below a specified limit value) the device transmits an alarm message to the remote monitoring device and to the patient management server to alert clinical personnel.

The telemetry transceiver 1150 allows drug delivery to be initiated or stopped by commands received from an external programmer or other device. The telemetry transceiver may also be used to wirelessly receive signals from other types of physiological monitoring devices. The controller may use such signals to control the delivery of drug therapy in a manner similar to the signals received from a sensor 1137. Also interfaced to the controller in FIG. 2 is a tactilely or magnetically actuated switch 1151 that may be used by the patient to initiate or stop the deliver of drug therapy. In certain embodiments, the controller may be programmed to deliver a specified dosage of the drug upon receiving a command to initiate delivery of drug therapy via the switch 1151. The controller may also be programmed to initiate drug therapy on command only if certain conditions are met such as the total amount of drug delivered over a certain period of time not exceeding a specified limit and one or more sensed physiological variables being within a specified range.

In certain embodiments, such as that illustrated in FIG. 1, the drug delivery catheter 1110 may include an occluding structure an inflatable balloon for blocking the antegrade flow of lymphatic fluid to allow delivery of the drug to the target location in a retrograde direction through the lymphatic vessel. FIG. 2 shows a balloon inflation apparatus 1113 interfaced to the controller that allows the balloon to be inflated during drug delivery through an inflation lumen of the catheter and deflated otherwise to allow normal lymphatic flow. Other embodiments may employ no occluding structure or may employ another type of actuated or passive occluding structure such as a tapered tip that is intubated within a lymph vessel to occlude flow.

Figure 3:
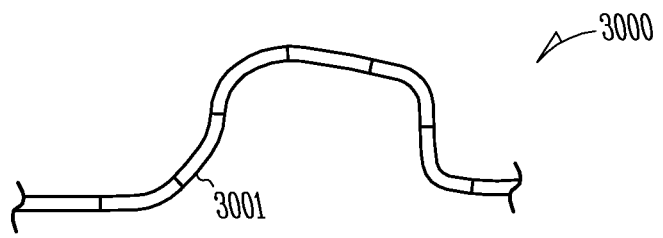
FIGS. 3 and 4A-B illustrate different embodiments of a drug delivery catheter.
Figure 4A:
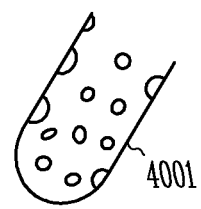
Figure 4B:
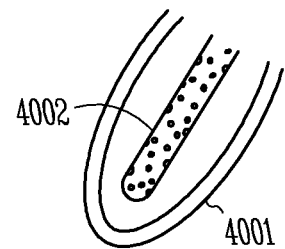

The catheter 1110 in one embodiment may also incorporate plurality of chambers that may be individually pressurized to effect selective stiffening of different portions of the catheter and facilitate passage of the catheter through a lymphatic vessel during implantation. FIG. 3 shows an example of such a catheter 3000 that includes a plurality of pressurizable chambers 3001 each of which communicates with a lumen in the catheter that may be connected to an external pressure source during the implantation procedure. In another embodiment, the drug delivery catheter comprises a plurality of concentric layers each of which is selectively permeable to different molecules to enable control of drug flow out of the catheter. FIG. 4A illustrates a partial view of such a catheter showing the outer layer 4001. FIG. 4B illustrates a partial sectional view of the catheter showing the inner layer 4002. A catheter having multiple layers with different permeabilities may also be used in conjunction with a chemosensor to sense the concentrations of different molecules in the lymphatic fluid.

Figure 5:
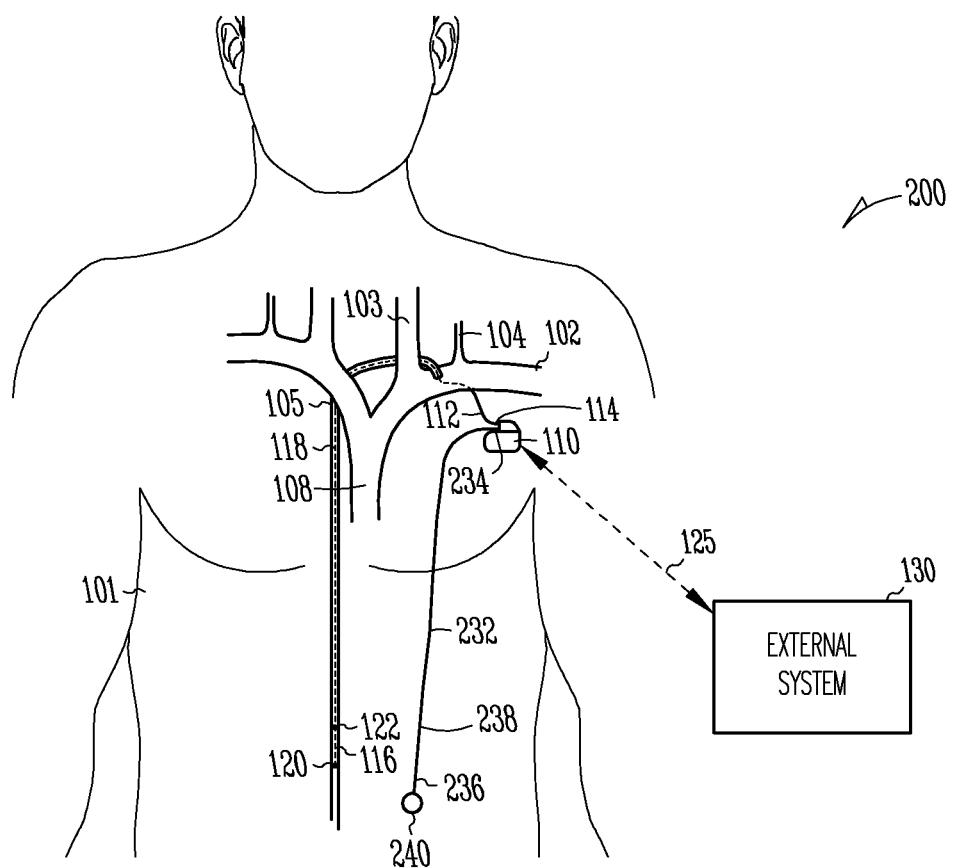
FIG. 5 shows an exemplary physical placement of an implantable drug delivery device.

FIG. 5 shows an exemplary physical placement within a body 101 of a system 200 for drug delivery via the lymphatic system that includes an implantable drug delivery device 110 that is placed subcutaneously on the patient's chest or abdomen, similar to a standard cardiac pacemaker. The implantable drug delivery device 110 communicates via a telemetry link 125 with an external system 130, such as an external programmer or remote monitoring unit and provides for access to implantable device 110 by a physician or other caregiver. In one embodiment, telemetry link 125 is an inductive telemetry link. In another embodiment, telemetry link 125 is a far-field radio-frequency (RF) telemetry link. Telemetry link 125 provides for data transmission from implantable device 110 to external system 130. This includes, for example, transmitting real-time physiological data acquired by implantable device 110, extracting physiological data acquired by and stored in implantable device 110, extracting patient history data such as occurrences of predetermined types of pathological events and therapy deliveries recorded in implantable device 110, and/or extracting data indicating an operational status of implantable device 110 (e.g., battery status and lead impedance). Telemetry link 125 also provides for data transmission from external system 130 to implantable medical device 110. This includes, for example, programming implantable device 110 to acquire physiological data, to perform at least one self-diagnostic test (such as for a device operational status), and/or to deliver one or more therapies and/or to adjust the delivery of one or more therapies. In certain embodiments, the implantable drug delivery device may also incorporate cardiac pacing and/or cardioversion/defibrillation functionality with leads and associated circuitry for that purpose. The implantable device may also be configured to deliver additional therapies such as cardiac resynchronization therapy (CRT) and cardiac remodeling control therapy (RCT).

The implantable drug delivery device 110 in this embodiment is connected to a drug delivery catheter 112, having a distal member that may incorporate a balloon or other structure for occluding a lymphatic vessel as described above. The catheter 112 passes subcutaneously from the device 110 to a point of venous access in the upper chest or neck such as the subclavian vein. As described below, the catheter may be positioned within the lymphatic system using a venous approach which involves initial entry into the venous blood system.

FIG. 5 also illustrates portions of the lymphatic and venous system including portions of thoracic duct 105, a subclavian vein 102, a left external jugular vein 103, and a left internal jugular vein 104. Thoracic duct 105 connects to subclavian vein 102 at the juncture of subclavian vein 102 and a left internal jugular vein 104. Lymphatic fluid from the lower body flows up to thoracic duct 105 and empties into the subclavian vein 102 from thoracic duct 105. The thoracic duct 105 is located in the posterior mediastinal area of the body 101, which is adjacent to the heart and includes various portions of the nervous system including portions of the vagus, sympathetic, and phrenic nerves. Thoracic duct 105 can also be used as a conduit for advancing the drug delivery catheter to a location in a lymphatic vessel from which a drug can be delivered to a target region of the body 101. Electrodes or other sensors incorporated into the catheter 112 may also be used to sense neural activity as well other physiological signals.

Catheter 112 includes a proximal end 114, a distal end 116, and an elongate catheter body 118 between proximal end 114 and distal end 116. Proximal end 114 is coupled to the implantable device 110. Distal end 116 includes at least one drug delivery port through which a drug may be injected into a lymphatic vessel. In the embodiment illustrated in FIG. 5, distal end 116 also includes electrodes 120 and 122 for sensing and/or stimulation. The implantable device 110 may include a hermetically sealed conductive housing that functions as a reference electrode. During the implantation of catheter 112, distal end 116 is inserted into subclavian vein 102 through an incision, advanced in subclavian vein 102 toward thoracic duct 105, inserted into thoracic duct 105 from subclavian vein 102, and advanced in thoracic duct 105 until a predetermined location in thoracic duct 105 or a lymphatic vessel communicating with the thoracic duct is reached.

Also shown in the illustrated embodiment is an additional lead 232 that includes a proximal end 234, a distal end 236, and an elongate lead body 238 between proximal end 234 and distal end 236. The lead 232 may be configured for subcutaneous placement, external to thoracic duct 105. Proximal end 234 is coupled to implantable device 110, and, in this embodiment, distal end 236 includes an electrode 240 that may be used for sensing and/or stimulation or for use as a reference electrode with any of the other electrodes of the implantable device 110.

The system and method described above for delivering agents via the lymphatic system makes use of an implantable device to delivery therapy on a more or less chronic basis. A similar catheter system may be used to deliver agents in an acute setting as well where an external device rather than an implantable device is used to deliver the agent through the catheter. In this embodiment, a one-time use catheter is positioned strategically in a lymphatic vessel. The distal tip may be configured to occlude normal lymphatic flow by either lodging in a smaller vessel or employing a balloon structure to inflate and occlude flow. After the agents have been deployed in the lymphatic vessel(s) the catheter is removed. This acute catheter system may be used, for example, to inject embolic material into portions of the thoracic duct that are ruptured and causing chylothorax. This condition sometimes occurs following thoracic surgery. The acute catheter system may also be used to locally treat lymphomas where it is used to inject chemotherapy directly to the tumor.

In order to implant a drug delivery catheter into a selected location within lymphatic vessel, the lymphatic system may be visualized using lymphangiography. In this technique, dye is injected into the subcutaneous tissue of an extremity such as the foot, or other peripheral lymph vessel, and the lymphatic system drains the dye making the lymphatic vessels visible. A lymphatic vessel is cannulated, and radiopaque contrast is injected to illuminate major lymph vessels including the thoracic duct and its ostium into the subclavian vein. The catheter may then be guided into the thoracic duct ostium via the venous system using fluoroscopy techniques and positioned at a selected location within the lymphatic system. Initial cannulation of the lymph ostium may be achieved through the left or right subclavian vein, the left jugular veins, or the femoral veins. In order to facilitate navigation through the lymphatic vessels and position the catheter at a selected anatomical location, an overlapping technique may be employed whereby fluoroscopic images produced by the injected dye are used in conjunction with anatomical images of the patient produced by other modalities such as conventional x-ray, CAT scans, MRI scans, or ultrasonic scans. The fluoroscopic image may be overlaid with the anatomical image and the catheter then guided to the selected location.

The catheter may be introduced into the venous system and from there into the thoracic duct ostium using conventional over-the-wire techniques that employ a guide wire. The guide wire is manually or mechanically pushed and manipulated to guide its travel and upon which catheters and/or leads may be advanced. A catheter having multiple pressurizable chambers such as described above may also be used to selectively stiffen portions of the catheter during implantation. A stereotaxis technique in which external magnets or other means are used to guide the catheter may also be used to improve maneuverability and precision as well as provide increased safety. An example of this technique is described in U.S. Pat. No. 6,475,223, hereby incorporated by reference. Once the catheter is in the lymphatic system, it must also traverse valves in the lymphatic vessels whose function is to allow flow of lymphatic fluid in only one direction to the thoracic duct. As the catheter is guided through a vessel to one of these valves, the catheter may incorporate a vacuum system to open the valves. When the vacuum system is actuated, it draws negative pressure to create a pressure gradient that opens the valve. An alternative technique for opening lymphatic valves involves using a catheter incorporating a compliant balloon on its distal tip. When the catheter reaches a lymphatic valve, the balloon is inflated to mechanically dilate the vessel which opens the valve and allows a wire or the catheter to pass through. This may be the same balloon used to occlude lymphatic flow during drug delivery as described above. In still another technique, the catheter incorporates an electrode at its tip (which may or may not be a lymphatic instrument intended to be left in the lymphatic vessel) that is used to cause smooth muscle contraction of the lymphatic vessel. Such smooth muscle contraction can create a pressure gradient that opens the valve and allows the catheter to advance past the valve.

Figure 6:
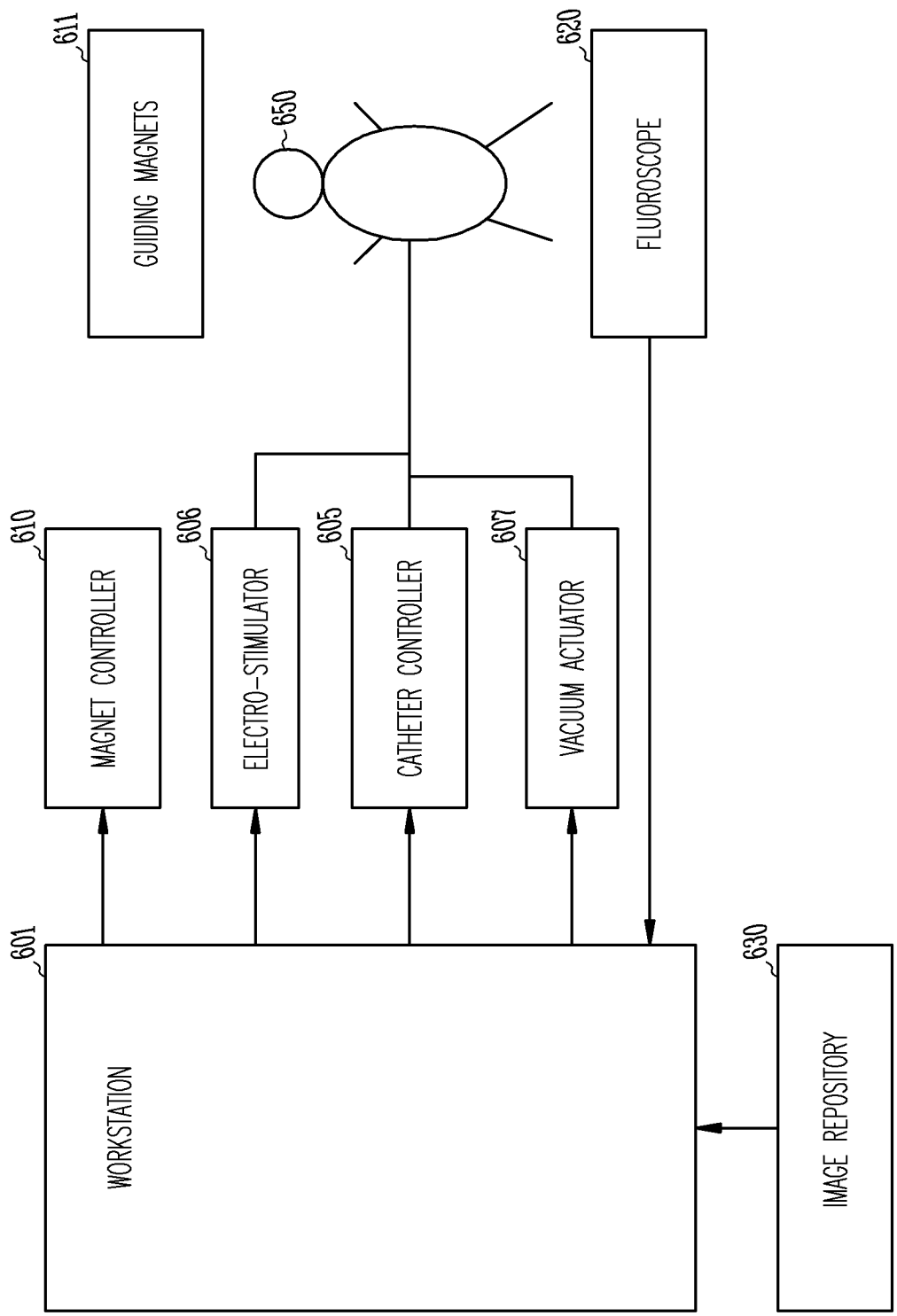
FIG. 6 shows an exemplary system for introducing a drug delivery catheter into the lymphatic system.

The implantation of a drug delivery catheter may be performed using the same techniques and apparatus as described in co-pending application Ser. No. 11/422,423 for implanting endolymphatic instrumentation. FIG. 6 shows an exemplary system for introducing a drug delivery catheter into the lymphatic system using the techniques described above. A system in accordance with the invention may have any or all of the components depicted in the figure. A workstation 601 is a computer in communication with the other system components and provides a user interface for controlling the operation of the system. The workstation provides an output for actuating the catheter controller 605 that mechanically pushes a drug delivery catheter 651 into the lymphatic system of patient 650. An electro-stimulator 606 and vacuum actuator 607 are also interfaced to the workstation for facilitating passage of the catheter 651 through valves in the lymph vessels. As described above, the electro-stimulator provides electrical energy to an electrode of the catheter 651 in order to cause contraction of smooth muscle in the lymphatic vessel walls and create a pressure gradient to open lymphatic valves. The vacuum actuator 607 draws a vacuum through a lumen of the catheter 651 in order to open lymphatic valves. The system also has the capability for magnetically guiding a ferromagnetic tip of the catheter 651 (or guide wire) by means of movable guiding magnets 611, and a magnet actuator 610 is interfaced to the workstation for this purpose. In order to provide the operator with information as to the location of the catheter within the lymphatic system, a fluoroscope 620 is interfaced to the workstation. When the patient's lymphatic system is injected with a radio-opaque dye through a port of the catheter, the fluoroscope provides images of the lymphatic vessels as the catheter travels therethrough. The workstation is also interfaced to an image repository 630 that stores images of the patient's anatomy obtained with one or more other imaging modalities such as conventional x-ray, CAT, MRI, and ultrasound. The operator may overlap an image from the image repository with the fluoroscopic image in order to provide anatomical landmarks for guiding the catheter to a selected location in the patient's body.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A device, comprising:
    an implantable housing;
    a drug delivery apparatus contained within the implantable housing;
    a catheter adapted for disposition within a lymphatic vessel and having a lumen communicating with the drug delivery apparatus;
    an occluding structure incorporated into the catheter for blocking flow of lymphatic fluid in the lymphatic vessel;
    a vacuum actuator for drawing a vacuum through a lumen of the catheter in order to create a pressure gradient within a lymphatic vessel and open lymphatic valves as the catheter is pushed therethrough; and,
    control circuitry contained within the implantable housing for controlling operation of the occluding structure and drug delivery apparatus to enable delivery of a drug out of the catheter distally from the occluding structure and into the lymphatic vessel.

2. The device of claim 1 wherein the occluding structure is an inflatable balloon mounted on the catheter and further comprising an inflation apparatus contained within the implantable housing for inflating the balloon through a balloon inflation lumen of the catheter.

3. The device of claim 1 wherein the catheter incorporates a plurality of chambers that may be individually pressurized to effect selective stiffening of different portions of the catheter and facilitate passage of the catheter through a lymphatic vessel.

4. The device of claim 1 further comprising a chemosensor for use in conjunction with selectively permeable concentric layers of the catheter to sense the concentrations of different molecules in the lymphatic fluid.

5. The device of claim 1 wherein the drug delivery apparatus is a mechanical pump connected to a drug reservoir.

6. The device of claim 1 further comprising sensing circuitry for sensing a physiological signal and wherein the control circuitry is configured to deliver the drug in a manner responsive to the physiological signal.

7. The device of claim 6 further comprising an electrode connected to the sensing circuitry by a lead adapted for disposition within the heart and wherein the sensing circuitry is configured to sense cardiac electrical activity.

8. The device of claim 6 further comprising a lymphatic sensor connected to the sensing circuitry for sensing the lymphatic fluid within the lymphatic vessel.

9. The device of claim 1 further comprising a tactilely or magnetically actuated switch operable to initiate or stop delivery of the drug.

10. The device of claim 1 further comprising a telemetry transceiver interfaced to the control circuitry for enabling wireless communication with the device.

11. A method for delivering a drug to a patient, comprising:
    implanting an implantable drug delivery device connected to a catheter;
    introducing the catheter into a lymphatic vessel of the patient;
    opening lymphatic valves by drawing a vacuum through a lumen of the catheter in order to create a negative pressure gradient within the lymphatic vessel;
    pushing the catheter through the lymphatic valves as they are opened by the negative pressure gradient;
    operating control circuitry within the implantable drug delivery device to deliver a drug through the catheter into the patient's lymphatic vessel.

12. The method of claim 11 further comprising:
    inflating a balloon mounted on the catheter to block antegrade flow of lymphatic fluid; and,
    delivering the drug out of the catheter distal to the balloon to enable retrograde flow of the drug through the lymphatic vessel.

13. The method of claim 11 further comprising individually pressurizing selected chambers of the catheter to effect selective stiffening of different portions of the catheter and facilitate passage of the catheter through a lymphatic vessel.

14. The method of claim 11 further comprising sensing a physiological signal and delivering the drug in a manner responsive to the physiological signal.

15. The method of claim 14 wherein the physiological signal is sensed by sensing circuitry within the implantable drug delivery device interfaced to the control circuitry.

16. The method of claim 15 further comprising sensing cardiac electrical activity with an electrode disposed within the heart and connected to the sensing circuitry by a lead and controlling the delivery of the drug in accordance therewith.

17. The method of claim 15 further comprising sensing the lymphatic fluid within the lymphatic vessel using a lymphatic sensor connected to the sensing circuitry and controlling the delivery of the drug in accordance therewith.

18. The method of claim 11 further comprising operating a tactilely or magnetically actuated switch operable to control delivery of the drug.

19. The method of claim 11 further comprising communicating with the control circuitry via telemetry to control delivery of the drug.

20. The method of claim 11 wherein the drug is selected from a group that consists of a pain relieving agent, a cancer chemotherapeutic agent, an anti-inflammatory agent, an embolizing agent, a cardiac drug, an antibiotic agent, a gene therapeutic agent, and a biological cellular agent.

* * * * *